US006071698A

United States Patent [19]
Beck

[11] Patent Number: 6,071,698
[45] Date of Patent: Jun. 6, 2000

[54] DNA EXTRACTION BUFFER AND METHOD OF USE THEREOF

[75] Inventor: James Joseph Beck, Cary, N.C.

[73] Assignee: Novartis Finance Corporation, New York, N.Y.

[21] Appl. No.: 08/968,505

[22] Filed: Nov. 12, 1997

Related U.S. Application Data

[62] Division of application No. 08/742,023, Nov. 1, 1996, Pat. No. 5,800,997.
[51] Int. Cl.[7] .............................. C12Q 1/68; C07H 21/00; C12P 19/34; C12N 5/02
[52] U.S. Cl. .............................. 435/6; 435/91.2; 435/410; 435/803; 536/25.4
[58] Field of Search .............................. 435/6, 91.2, 410, 435/803; 536/25.4

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,828,890 | 5/1989 | Tiedeman | 428/22 |
| 5,324,632 | 6/1994 | Weisburg et al. | 435/6 |
| 5,338,745 | 8/1994 | Fukazawa | 514/330 |
| 5,447,848 | 9/1995 | Barns et al. | 435/29 |
| 5,558,996 | 9/1996 | Bartlett | 435/7.31 |
| 5,585,238 | 12/1996 | Ligon et al. | 435/6 |
| 5,612,208 | 3/1997 | Nakanishi | 435/189 |
| 5,834,250 | 11/1998 | Wells | 435/7.1 |
| 5,871,975 | 2/1999 | Kacian | 435/91.2 |

FOREIGN PATENT DOCUMENTS

WO 91/14001 9/1991 WIPO.
WO 95/24260 11/1995 WIPO.

OTHER PUBLICATIONS

Cheung,W. et al. PCR Methods and Applications 3(1):69–70, 1993.
Chunwongse, J. et al. Theor. Appl. Genet. 86:694–698, 1993.
Kreader, C. Appl. Envir. Midrobiol. 62(3):1102–1106, Mar. 1996.
Sigma Catalog, p. 62–65, 1993.
Steiner, J.J. et al. Nucleic Acids Research 23(13):2569–2570, Jul. 1995.
Basha, S.Y. et al. Current Science 68(6):587–588, Apr. 1995.
Bentolila, et al., "Identification of an RFLP marker tightly linked to the Ht1 gene in maize", *Theo. Appl. Genet*, 82:393–398 (1991).
Johanson et al. "Use of PCR for detection of *Mycosphaerella fijiensis* and *M. musicola*, the causal agents of Sigatoka leaf spots in banana and plantain", *Mycol. Res.*, 97:670–674 (1993).

Hung et al., "A specificity enhancer for polymerase chain reaction", *Nucleic Acids Research*, 18(16): 4953 (1990).
Klimyuk et al., "Alkali treatment for rapid preparation of plant material for reliable PCR analysis", *The Plant Journal*, 3(3): 493–494 (1993).
Nazar, R.N., et al, "Potential use of PCR–amplified ribosomal intergenic sequences in the detection and differentiation of verticillium wilt pathogens", *Physiol. and Molec. Plant Pathol.*, 39:1–11 (1991).
Oliver et al., "Amplification and sequencing of ribosomal DNA ITS regions for specific detection of *Helminthosporium solani*", *Phytopathology* 86(11) pp. S1 and S12 (Supplement) (1996).
Poupard et al., "Molecular characterization of *Pseudocercosporella herpotrichoides* isolates by amplification of ribosomal DNA internal transcribed spaces", *Plant Pathology*, 42: 873–881 (1993).
Schesser et al., "Use of Polymerase Chain Reaction To Detect the Take–All Fungus, *Gaeumannomyces graminis*, in Infected Wheat Plants", *Applied and Environ. Microbiol.*, 57(2):553–556 (1991).
Stratagene Catalog, 1988, p. 39.
Tisserat et al., "Selective Amplification of rDNA Internal Transcribed Spacer Regions to Detect *Ophiosphaerella korrae* and *O. herpotricha*", *Phytopathology*, 84(5): 478–482 (1994).
Wang, et al., "A simple method of preparing plant samples for PCR", *Nucleic Acids Research*, 21(17): 4153–4154 (1993).
White, T.J., et al., "Amplification and Direct Sequencing of Fungal Ribosomal RNA Genes for Phylogenetics", In: *PCR Protocols*; Academic Press Inc., pp. 315–322 (1990).
GenBank Accession No. L08734, computer printout, Feb. 5, 1993.
Xue et al., "Pathotype identification of *Leptosphaeria maculans* with PCR and oligonucleotide primers from ribosomal internal transcribed spacer sequences", *Physiological and Molecular Plant Pathology*, 179–188 (1992).

*Primary Examiner*—Carla J. Myers
*Assistant Examiner*—Diana Johannsen
*Attorney, Agent, or Firm*—J. Timothy Meigs

[57] ABSTRACT

Internal Transcribed Spacer (ITS) DNA sequences from the ribosomal RNA gene region are described for different species and strains of *Helminthosporium carbonum*, *Helminthosporium turcicum*, *Helminthosporium maydis*, *Cercospora zeae-maydis*, *Kabatiella zeae* and *Puccinia sorghi*. Specific primers from within these sequences are identified as being useful for the identification of the fungal isolates using PCR-based techniques. Also described is a novel extraction buffer solution for use in isolating DNA from an organism.

19 Claims, No Drawings

DNA EXTRACTION BUFFER AND METHOD OF USE THEREOF

This is a divisional of Ser. No. 08/742,023, filed Nov. 1, 1996 now U.S. Pat. No. 5,800,997.

FIELD OF THE INVENTION

The present invention relates to the use of species-specific primers in polymerase chain reaction assays for the detection of fungal pathogens of maize. The use of these primers enables the detection of specific isolates of fungal pathogens and the monitoring of disease development in plant populations. The present invention also relates to a novel extraction buffer solution for use in isolating DNA from an organism.

BACKGROUND OF THE INVENTION

Diseases in plants cause considerable crop loss from year to year resulting both in economic deprivation to farmers and, in many parts of the world, to shortfalls in the nutritional provision for local populations. The widespread use of fungicides has provided considerable security against plant pathogen attack. However, despite $1 billion worth of expenditure on fungicides, worldwide crop losses amounted to approximately 10% of crop value in 1981 (James, 1981; *Seed Sci. & Technol.* 9: 679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains that are resistant to particular fungicides. As early as 1981, Fletcher and Wolfe (1981; *Proc. 1981 Brit. Crop Prot. Conf.*) contended that 24% of the powdery mildew populations from spring barley and 53% from winter barley showed considerable variation in response to the fungicide triadimenol and that the distribution of these populations varied between varieties, with the most susceptible variety also giving the highest incidence of less susceptible types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and *Mycosphaerella fijiensis* to triazoles to mention just a few (Jones and Clifford; Cereal Diseases, John Wiley, 1983).

The three most important cereal crops in the world are maize (corn), rice and wheat (1973; Compendium of Corn Diseases, Amer. Phytopath. Soc. page 1). There are a great number of fungi, bacteria, and viruses that are pathogenic to maize, causing 9.4 % annual worldwide losses. In the corn belt of the United States, maize reduction because of disease infection is between 7 to 17% annually. Maize is the most important native American plant, and the U.S. produces about 44% of the world's 250 million metric tons annual production.

The major infectious diseases of maize are caused by fungi and include rusts, smuts, downy mildews, rots, spots, blights and deformations (1973; Compendium of Corn Diseases, Amer. Phytopath. Soc. page 13). Although fungal diseases are usually diagnosed by the structures produced by the pathogens, the differential symptomology caused by different isolates and species of these fungi make the accurate predictive determination of potential disease loss difficult. Consequently, the availability of improved diagnostic techniques for the rapid and accurate identification of specific pathogens will be of considerable use to field pathologists.

There are three primary species of Helminthosporium pathogenic to maize causing foliar diseases. *Helminthosporium carbonum* causes helminthosporium leaf spot (blight), also known as northern leaf spot (1973; Compendium of Corn Diseases, Amer. Phytopath. Soc. page 17). It is distributed throughout the Americas, southeast Asia, southeast Europe, south and central Africa, and India (Jones and Clifford; Cereal Diseases, John Wiley, 1983). There are two primary physiologically-based races. Race 1 is highly virulent on maize, causing a charred appearance on the ear's kernels. Race 2 tends to be less virulent than race 1 and does not diplay host specificity. Race 2 produces a host-specific toxin. *Helminthosporium maydis* causes southern leaf blight in maize. It occurs worldwide in warm (20–32° C.), humid climates. In the United States, it is found in the southeastern and midwestern states (Jones and Clifford; Cereal Diseases, John Wiley, 1983). The disease was originally thought to be of little economic importance until a severe 1970 epidemic in the U.S. resulted in large losses. Northern leaf blight (*turcicum* leaf blight) is caused by *Helminthosporium turcicum*. The disease develops in humid areas of the world where maize is grown (1973; Compendium of Corn Diseases, Amer. Phytopath. Soc. page 16). Moderate temperatures (18–27° C.) and heavy dews during the growing season promote severe disease development in which 50% losses of grain can occur. Typical control of these diseases include the use fungicides, crop rotation, burning crop debris, and breeding resistant hybrids and varieties.

*Kabateilla zeae* is another significant maize foliar pathogen causing eyespot disease. The disease originally reported as brown eyespot in Japan has also been found in Canada, Argentina, Austria, France, Germany, Yugoslavia, New Zealand and in several north-central U.S. states and Pennsylvania (1973; Compendium of Corn Diseases, Amer. Phytopath. Soc. page 21). The disease may develop on sheaths and outer husks, but lesions are more concentrated on leaves approaching maturity. In extremely infected plants, kernel infections may also develop. Cool, humid weather favors disease development. Disease control measures include the use of less susceptible hybrids, fungicides, and clean plowing or crop rotation.

Cercospora or gray leaf spot is caused by *Cercospora zeae-maydis* and infects maize, barnyardgrass, Johnsongrass and other Sorghum species (1973; Compendium of Corn Diseases, Amer. Phytopath. Soc. page 24). The disease is prevalent in warm-to-hot, humid areas of the United States, Mexico, Central America, northern South America, Europe, Africa, southeast Asia, India, China, and the Philippines. The disease has increased in severity in recent years in the southeastern and mid-Atlantic states of the U.S. especially in areas using minimum tillage of maize and no crop rotation (Latterell and Rossi, 1983; *Plant Disease.* Vol. 67, No. 8: 842–847). The disease can spread from the leaf sheaths to the stalk in highly infected plants. This can cause stalk deterioration to the point where lodging precludes mechanical harvesting. Crop rotation, resistant cultivars and fungicides are currently used to control gray leaf spot.

*Puccinia sorghi* causes common maize rust and can be found wherever maize is grown. Infection can occur on any plant parts above ground but is mainly found on the leaves (1973; Compendium of Corn Diseases, Amer. Phytopath. Soc. page 24). Cooler temperatures (16–23 ° C.) and high moisture contribute to the proliferation of the disease. Under severe infection conditions, chlorosis and death of the leaves and sheaths may occur ultimately reducing cereal yield.

Thus, there is a real need for the development of technology that will allow the identification of specific races of pathogen fungi early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

Additionally, with the increasing need for DNA fingerprinting, restriction fragment length polymorphism (RFLP) analysis, Southern transfers and PCR analysis, the isolation of high molecular weight DNA becomes a major problem when attempting to process a large number of plant samples in a timely manner. Several methods for the isolation of DNA have been reported, all of which have drawbacks for various reasons. These include DNA losses due to degradation and adsorption, the co-isolation of PCR inhibiting contaminants and labor extensive and costly protocols. Therefore, there is a need for a DNA extraction method which isolates high molecular weight DNA for high throughput analysis using molecular biology methods.

SUMMARY OF THE INVENTION

The present invention is drawn to methods of identification of different pathotypes of plant pathogenic fungi. The invention provides Internal Transcribed Spacer (ITS) DNA sequences that show variability between different fungal pathotypes. In a preferred embodiment, the invention provides ITS1 and ITS2 DNA sequences for the pathogens *Helminthosporium carbonum, Helminthosporium turcicum, Helminthosporium maydis, Cercospora zeae-maydis, Kabatiella zeae*, and *Puccinia sorghi*. Such DNA sequences are useful in the method of the invention as they can be used to derive primers for use in polymerase chain reaction (PCR)-based diagnostic assays. These primers generate unique fragments in PCR reactions in which the DNA template is provided by specific fungal pathotypes and can thus be used to identify the presence or absence of specific pathotypes in host plant material before the onset of disease symptoms.

This invention provides the possibility of assessing potential damage in a specific crop variety-pathogen strain relationship and of utilizing judiciously the diverse armory of fungicides which is available. Furthermore, the invention can be used to provide detailed information on the development and spread of specific pathogen races over extended geographical areas. The invention provides a method of detection that is especially suitable for diseases with a long latent phase. In addition, a method is described for extracting DNA from plant tissue for high throughput PCR analysis.

Kits useful in the practice of the invention are also provided. The kits find particular use in the identification of the pathogens Helminthosporium carbonum, *Helminthosporium turcicum, Helminthosporium maydis, Cercospora zeae-maydis, Kabatiella zeae*, and *Puccinia sorghi.*

BRIEF DESCRIPTION OF THE SEQUENCES IN THE SEQUENCE LISTING

SEQ ID NO:1 DNA sequence of the ITS region from *Cercospora zeae-maydis*isolate #Ladder 3-1 (clone pCRCZLAD3-1(4-3)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:2 DNA sequence of the ITS region from *Cercospora zeae-maydis*isolate #POS 12 (clone pCRCZMPOS12(2-1)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:3 DNA sequence of the ITS region from *Kabatiella zeae* isolate #56351 (clone pCRKZ56351(5-1)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:4 DNA sequence of the ITS region from *Helminthosporium maydis* isolate #24772 (clone pCRHMAY24772(2-1)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:5 DNA sequence of the ITS region from *Helminthosporium maydis* isolate #11534 (clone pCRHMAY11534(4-1)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:6 DNA sequence of the ITS region from *Helminthosporium turcicum* isolate #26306 (clone pCRHTUR26306(3-1)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:7 DNA sequence of the ITS region from *Helminthosporium carbonum* isolate #16185 (clone CRHCAR16185(5-2)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:8 DNA sequence of the ITS region from *Puccinia sorghi* (GenBank accession #L08734), comprising in the 5' to 3' direction: partial sequence of Internal Transcribed Spacer 1, 5.8S rRNA gene, Internal Transcribed Spacer 2, and 5' end of large subunit rRNA gene.

SEQ ID NO:9 Oligonucleotide Primer ITS1.

SEQ ID NO:10 Oligonucleotide Primer ITS2.

SEQ ID NO:11 Oligonucleotide Primer ITS3.

SEQ ID NO:12 Oligonucleotide Primer ITS4.

SEQ ID NO:13 M13 Universal-20 Primer.

SEQ ID NO:14 Reverse Primer used in Example 2.

SEQ ID NO:15 Oligonucleotide Primer JB586.

SEQ ID NO:16 Oligonucleotide Primer JB587.

SEQ ID NO:17 Oligonucleotide Primer JB588.

SEQ ID NO:18 Oligonucleotide Primer JB589.

SEQ ID NO:19 Oligonucleotide Primer JB590.

SEQ ID NO:20 Oligonucleotide Primer JB591.

SEQ ID NO:21 Oligonucleotide Primer JB592.

SEQ ID NO:22 Oligonucleotide Primer JB593.

SEQ ID NO:23 Oligonucleotide Primer JB594.

SEQ ID NO:24 Oligonucleotide Primer JB595.

SEQ ID NO:25 Oligonucleotide Primer JB596.

SEQ ID NO:26 Oligonucleotide Primer JB597.

SEQ ID NO:27 Oligonucleotide Primer JB598.

SEQ ID NO:28 Oligonucleotide Primer JB615.

SEQ ID NO:29 Oligonucleotide Primer JB616.

SEQ ID NO:30 Oligonucleotide Primer JB617.

SEQ ID NO:31 Oligonucleotide Primer JB618.
SEQ ID NO:32 Oligonucleotide Primer JB619.
SEQ ID NO:33 Oligonucleotide Primer JB620.
SEQ ID NO:34 Oligonucleotide Primer JB621.
SEQ ID NO:35 Oligonucleotide Primer JB622.
SEQ ID NO:36 Oligonucleotide Primer JB623.
SEQ ID NO:37 Oligonucleotide Primer JB624.
SEQ ID NO:38 Oligonucleotide Primer JB625.
SEQ ID NO:39 Oligonucleotide Primer JB626.
SEQ ID NO:40 Oligonucleotide Primer JB627.
SEQ ID NO:41 Oligonucleotide Primer JB628.

DETAILED DESCRIPTION OF THE INVENTION

The present invention provides unique DNA sequences that are useful in identifying different pathotypes of plant pathogenic fungi. Particularly, the DNA sequences can be used as primers in PCR-based analysis for the identification of fungal pathotypes. The DNA sequences of the invention include the Internal Transcribed Spacer (ITS) sequences of the ribosomal RNA gene regions of particular fungal pathogens as well as primers derived from these regions that are capable of identifying the particular pathogen. These ITS DNA sequences from different pathotypes within a pathogen species or genus, which vary between the different members of the species or genus, can be used to identify those specific members.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen mitochondrial genome (Schlesser et al., 1991; *Applied and Environ. Microbiol.* 57: 553–556), and random amplified polymorphic DNA (i.e. RAPD) markers were able to distinguish numerous races of *Gremmeniella abietina*, the causal agent of scleroderris canker in conifers. More recently, primers from within DNA sequences from the ITS of the ribosomal RNA gene region of strains of Septoria, Pseudocercosporella, Fusarium, and Mycosphaerella have been identified as being useful for the identification of the fungal isolates using PCR-based techniques (WO 95/29260, herein incorporated by reference in its entirety.)

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units, each of which encodes three mature subunits of 18S (small subunit), 5.8S, and 28S (large subunit). These subunits are separated by two Internal Transcribed Spacers, ITS1 and ITS2, of around 300 bp (White et al., 1990; In: PCR Protocols; Eds.: Innes et al.; pages 315–322). In addition, the transcriptional units are separated by non-transcribed spacer sequences (NTSs). The ITS and NTS sequences are particularly suitable for the detection of specific pathotypes of different fungal pathogens.

The DNA sequences of the invention are from the Internal Transcribed Spacer sequences of the ribosomal RNA gene region of different plant pathogens. The ITS DNA sequences from different pathotypes within a pathogen species or genus vary among the different members of the species or genus. Once having determined the ITS sequences of a pathogen, these sequences can be aligned with other ITS sequences. In this manner, primers can be derived from the ITS sequences. That is, primers can be designed based on regions within the ITS sequences that contain the greatest differences in sequence among the fungal pathotypes. These sequences and primers based on these sequences can be used to identify specific pathogens.

Particular DNA sequences of interest include ITS1 and ITS2 DNA sequences from *Helminthosporium carbonum, Helminthosporium turcicum, Helminthosporium maydis, Cercospora zeae-maydis, Kabatiella zeae* and *Puccinia sorghi*. Examples of such ITS DNA sequences are disclosed in SEQ ID Nos: 1–8. However, isolates of these organisms other than the isolates described herein may have minor sequence variations in their ITS regions. The present invention is intended to encompass the ITS DNA sequences of any isolates of these fungal pathogens. Sequences of oligonucleotide primers of interest are disclosed in SEQ ID Nos: 9–41. The sequences find use in the PCR-based identification of the pathotypes of interest.

Methods for the use of the primer sequences of the invention in PCR analysis are well known in the art. For example, see U.S. Pat. Nos. 4,683,195 and 4,683,202, as well as Schlesser et al. (1991) *Applied and Environ. Microbiol*. 57:553–556. See also, Nazar et al. (1991*; Physiol. and Molec. Plant Pathol*. 39: 1–11), which used PCR amplification to exploit differences in the ITS regions of *Verticillium albo-atrum* and *Verticillium dahliae* and therefore distinguish between the two species; and Johanson and Jeger (1993*; Mycol. Res*. 97: 670–674), who used similar techniques to distinguish the banana pathogens *Mycosphaerella fijiensis* and *Mycospharella musicola.*

The ITS DNA sequences of the invention can be cloned from fungal pathogens by methods known in the art. In general, the methods for the isolation of DNA from fungal isolates are known. See, Raeder & Broda (1985) *Letters in Applied Microbiology* 2:17–20; Lee et al. (1990) *Fungal Genetics Newsletter* 35:23–24; and Lee and Taylor (1990) In: *PCR Protocols: A Guide to Methods and Applications*, Innes et al. (Eds.); pages 282–287.

Alternatively, the ITS sequences of interest can be determined by PCR amplification. In an exemplified embodiment, primers to amplify the entire ITS sequence were designed according to White et al. (1990; In: PCR Protocols; Eds.: Innes et al. pages 315–322), and the amplified ITS sequence was subcloned into the pCRII cloning vector. The subcloned sequence included the left hand ITS (ITS1), the right hand ITS (ITS2), as well as the centrally located 5.8S rRNA gene. This was undertaken for *Helminthosporium carbonum, Helminthosporium turcicum, Helminthosporium maydis, Cercospora zeae-maydis*, and *Kabatiella zeae.*

The ITS sequences were determined and the sequences were compared within each pathogen group to locate divergences that might be useful to test in PCR to distinguish the different species and/or strains. The ITS DNA sequences that were determined are shown in SEQ ID Nos: 1–7 as well as in FIGS. 1–6. From the identification of divergences, numerous primers were synthesized and tested in PCR-amplification. Templates used for PCR-amplification testing were firstly purified pathogen DNA, and subsequently DNA isolated from infected host plant tissue. Thus, it was possible to identify pairs of primers that were diagnostic, i.e. that identified one particular pathogen species or strain but not another species or strain of the same pathogen.

Preferred primer combinations are able to distinguish between the different species or strains in infected host tissue, i.e. host tissue that has previously been infected with a specific pathogen species or strain. This invention provides numerous primer combinations that fulfill this criterion for different *Helminthosporium carbonum, Helminthosporium turcicum, Helminthosporium maydis, Cercospora zeae-maydis, Kabatiella zeae*, and *Puccinia sorghi*. The primers of the invention are designed based on sequence differences among the fungal ITS regions. A minimum of one base pair difference between sequences can permit design of a discriminatory primer. Primer, designed to a specific fungal DNA's ITS region can be used in combination with a primer made to a conserved sequence region within the ribosomal DNA's coding region to amplify species-specific PCR fragments. In general, primers should have a theoretical melting temperature between about 60 to about 70 degree ° C. to achieve good sensitivity and should be void of significant secondary structure and 3' overlaps between primer combinations. Primers are generally at least about 5–10 nucleotide bases long.

The present invention lends itself readily to the preparation of "kits" containing the elements necessary to carry out the process. Such a kit may comprise a carrier being compartmentalized to receive in close confinement therein one or more container, such as tubes or vials. One of the containers may contain unlabeled or detectably labeled DNA primers. The labeled DNA primers may be present in lyophilized form or in an appropriate buffer as necessary. One or more containers may contain one or more enzymes or reagents to be utilized in PCR reactions. These enzymes may be present by themselves or in mixtures, in lyophilized form or in appropriate buffers.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The examples below show typical experimental protocols that can be used in the isolation of ITS sequences, the selection of suitable primer sequences, the testing of primers for selective and diagnostic efficacy, and the use of such primers for disease and fungal isolate detection. Such examples are provided by way of illustration and not by way of limitation.

EXAMPLES

Standard recombinant DNA and molecular cloning techniques used here are well known in the art and are described by J. Sambrook, E. F. Fritsch and T. Maniatis, *Molecular Cloning: A Laboratory manual*, Cold Spring Harbor laboratory, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Miolecular Biology*, pub. by Greene Publishing Assoc. and Wiley-Interscience (1987).

Example 1

Fungal Isolates and Genomic Fungal DNA Extraction

See Table 1 for a listing of the fungal isolates used and their source. Fungi except for *Puccina sorghi* were grown in 150 ml potato dextrose broth inoculated with mycelial fragments from PDA (Potato Dextrose Agar) cultures. Cultures were incubated on an orbital shaker at 28° C. for 7–11 days. Mycelia were pelleted by centrifugation and then ground in liquid nitrogen and total genomic DNA extracted using the protocol of Lee and Taylor (1990; In: *PCR Protocols: A Guide to Methods and Applications*; Eds.: Innes et al.; pages 282–287). Since *P. sorghi* is an obligate biotroph and could therefore not be cultured on PDA, DNA was isolated from its spores from an infected maize leaf and ground with a Kontes pestle.

TABLE 1

Source of Test Isolates

| Fungus | Isolate | Origin | Source |
|---|---|---|---|
| Helminthosporium maydis[1] | 6921 | Illinois | C. Naidoo[2] |
| Helminthosporium maydis | XXXX | Illinois | C. Naidoo |
| Helminthosporium maydis | 5654 | Illinois | C. Naidoo |
| Helminthosporium maydis | 11534 | Maryland | ATCC[3] |
| Helminthosporium maydis | 4709 | Indiana | C. Naidoo |
| Helminthosporium maydis, Race t, mating type A | 24772 | North Carolina | ATCC[3] |
| Helminthosporium turcicum[4] | 6810 | Iowa | C. Naidoo |
| Helminthosporium turcicum | 6830 | Minnesota | C. Naidoo |
| Helminthosporium turcicum, Race 2 | 6402 | Illinois | C. Naidoo |
| Helminthosporium turcicum | 6870 | Texas | C. Naidoo |
| Helminthosporium turcicum, Race 1 | 6586 | Illinois | C. Naidoo |
| Helminthosporium turcicum | 26306 | Illinois | ATCC |
| Helminthosporium turcicum, Race 2 | 6294 | Indiana | C. Naidoo |
| Helminthosporium turcicum, Race 2 | 5352 | Ohio | C. Naidoo |
| Helminthosporium carbonum[5] | 5870 | Illinois | C. Naidoo |
| Helminthosporium carbonum | 6164 | Iowa | C. Naidoo |
| Helminthosporium carbonum | 6330 | Nebraska | C. Naidoo |
| Helminthosporium carbonum | 6378 | Iowa | C. Naidoo |
| Helminthosporium carbonum | 16185 | Virginia | ATCC |
| Kabatiella zeae | 18594 | Wisconsin | ATCC |
| Kabatiella zeae | 5125 | Indiana | C. Naidoo |
| Kabatiella zeae | 56344 | Wisconsin | ATCC |
| Kabatiella zeae | 56351 | Michigan | ATCC |
| Kabatiella zeae | 6823 | Minnesota | C. Naidoo |
| Cercospora zeae-maydis | 5860 | Illinois | C. Naidoo |
| Cercospora zeae-maydis | 6939 | Ohio | C. Naidoo |
| Cercospora zeae-maydis | 6911 | Illinois | C. Naidoo |
| Cercospora zeae-maydis | 6928 | Illinois | C. Naidoo |
| Cercospora zeae-maydis | SKIN11 | Indiana | L. Dunkle[6] |
| Cercospora zeae-maydis | Ladder 3-1 | Indiana | L. Dunkle |
| Cercospora zeae-maydis | POS12 | Indiana | L. Dunkle |
| Macrophomina phaseolina | 103 | Kansas | J. Mihail[7] |
| Macrophomina phaseolina | 97 | St. Charles, MO | J. Mihail |
| Aspergillus flavus | NRRL3557 | — | G. Payne[8] |
| Fusarium moniliforme | 6354 | Illinois | C. Naidoo |
| Diplodia maydis | 5139 | Iowa | C. Naidoo |
| Puccinia sorghi | IL | Illinois | C. Naidoo |
| Puccinia sorghi | MI | Michigan | C. Naidoo |
| Puccinia sorghi | IL88 | Illinois | C. Naidoo |
| Puccinia sorghi | VA | Virginia | C. Naidoo |
| Puccinia polyspora | TX96 | Texas | C. Naidoo |

[1]Syn. *Bipolaris maydis, Drechslera maydis*
[2]Dr. Charmaine Naidoo, Ciba Seeds Research, Bloomington, Illinois USA
[3]American Type Culture Collection, Rockville, Maryland USA
[4]Syn. *Exserohilum turcicum, Bipolaris turcica, Drechslera turcica*
[5]Syn. *Drechslera zeicola, Bipolaris zeicola*
[6]Dr. Larry Dunkle, Purdue University, West Lafayette, Indiana USA
[7]Dr. Jeanne Mihail, University of Missouri-Columbia, Columbia, Missouri USA
[8]Dr. Gary Payne, North Carolina State University, Raleigh, North Carolina USA

Example 2
Isolation of the Internal Transcribed Spacer (ITS) Regions

The approximately 600 bp internal transcribed spacer region fragments were PCR amplified from 10 ng of genomic DNA isolated from *H. turcicum* isolates 6586, 26306 and 6402, *H. maydis* isolates 6921, 11534 and 24772, *H. carbonum* isolates 5870 and 16185, *K. zeae* isolates 56351, 18594 and 5125 and *C. zeae-maydis* isolates 5860, POS12 and Ladder 3-1 using 50 pmol of primers ITS1 (5' TCCGTAGGTGAACCTGCGG-3'; SEQ ID NO:9) and ITS4 (5'-TCCTCCGCTTATTGATATGC-3'; SEQ ID NO:12). PCRs were performed as described in Example 4. PCR products were purified using Promega's Wizard DNA Clean-up kit (Madison, Wis.). The DNA sequences of the ITS regions were determined by the dideoxy method using the Applied Biosystems (Foster City, Calif.) automated sequencer with the primers ITS1 (SEQ ID NO:9), ITS2 (5'-GCTGCGTTCTTCATCGATGC-3'; SEQ ID NO:10), ITS4 (SEQ ID NO:12) and the M13 universal-20 (5'-GTAAAACGACGGCCAGT-3';SEQ ID NO:13) and Reverse (5'-AACAGCTATGACCATG-3'; SEQ ID NO:14) primers. The ITS primers ITS1, ITS2, ITS3, and ITS4 used are detailed in White et al. (1990; In: PCR Protocols; Eds.: Innes et al. pages 315–322). PCR products from amplifications using *H. turcicum* isolate 26306, *H. maydis* isolates 11534 and 24772, *Kabatiella zeae* isolate 56351, *H. carbonum* isolate 16185, and *C. zeae-maydis* isolates POS12 and Ladder 3-1 were cloned using the Invitrogen Corporation's (San Diego, Calif.) TA Cloning Kit (part no. K2000-01) using the pCRII or PCR2.1 cloning vector.

Example 3
DNA Extraction from Maize Leaves

DNA was extracted from maize leaves by using either a modified version of the Rapid DNA Extraction protocol from the MicroProbe Corporation's (Garden Grove, Calif.) IsoQuick Nucleic Acid Extraction Kit (cat# MXT-020-100) or by a bulk leaf maceration method. The Isoquick protocol was used to extract highly purified DNA from fungal-inoculated maize leaves for assay validation purposes. Typical yields using the IsoQuick kit were 5–10 μg of total DNA from 0.2 g of leaf tissue from which approximately 100 ng of total DNA were used in each PCR assay.

The bulk leaf maceration method was used to isolate DNA from several naturally infected maize leaves from the field to optimize the leaf field sampling method for high throughput analysis. In step 2 of this method, "Muller Extraction Buffer" is used. The potential concentration ranges of the ingredients of the Muller Extraction Buffer are as follows:

0–2.0 % w/v Tween-80
0–2.0 M Tris-Cl, pH 6–8
0–2.0 M NaCl
0–2 % BSA
0–2 % sodium azide
0–500 mM EDTA
0–2 % w/v tartrazin However, in the preferred embodiment of the bulk leaf maceration method, the following recipe is used: 0.1% w/v Tween-80; 0.04 M Tris-Cl, pH 7.7; 0.15 M NaCl; 0.1% w/v BSA-Pentex fraction V; 0.01% w/v sodium azide; 200 mM EDTA. The color dye tartrazin may optionally be added as well.

Modified Rapid DNA Extraction:

Before using the kit for the first time, the entire contents of Reagent 2A (20×Dye Concentrate) were added to Reagent 2 (Extraction Matrix).

(1) Approximately 0.2 g of leaf sample were added to a 1.5 ml eppendorf tube containing 50 μl sample buffer A and 50 μl #1 lysis solution. The leaf sample was ground with a Kontes pestle.

(2) Reagent 2 (Extraction Matrix) was shaken vigorously. 350 μl of reagent 2 was added to the sample lysate.

(3) 200 μl of Reagent 3 were added (Extraction Buffer) to the sample. The sample was vortexed 20 sec.

(4) Microcentrifugation at 12,000×g for 5 min.

(5) The aqueous phase (upper layer) was transferred to a new microcentrifuge tube. This volume was typically about 200 μl.

(6) 0.1×the volume of the aqueous phase of Reagent 4 (Sodium Acetate) was transferred to the aqueous phase sample.

(7) An equal volume of isopropanol was added to the aqueous phase sample followed by vortexing.

(8) Microcentrifugation at 12,000×g for 10 min.

(9) The supernatant was discarded without disturbing the nucleic acid pellet. 0.5 ml of −20° C. 70% ethanol was added to the pellet. The tube was vortexed to mix.

(10) Microcentrifugation at 12,000×g for 5 min.

(11) The supernatant was discarded and the pellet was allowed to dry.

(12) The nucleic acid pellet was dissolved in 50 μl TE with 100 μg/ml Rnase A.

Bulk Leaf Maceration Method:

(1) Took a random sampling of an appropriate number of leaves from a population of maize plants.

(2) Placed the leaves in a Bioreba (Reinach, Switzerland) heavy duty plastic bag (cat#490100). Weighed the plant tissue, plastic bag with leaves minus the tare (weight of the plastic bag).

(3) Added an equal volume (ml) of Muller Extraction Buffer per weight (g) of leaf tissue. Macerated the tissue using a Bioreba Homex 6 homogenizer set at 70. Ground the leaves until the tissue was fibrous.

(4) Removed maceration juice (extract) from the macerated tissue/extraction buffer.

(5) Pooled the extracts from multiple bags, if used, and vortexed well. Aliquoted the extraction juice into eppendorf tubes on ice.

(6) Boiled 100 μl of the concentrated extract for 5 minutes.

(7) Placed the boiled extract on ice.

(8) Made a 1:10 dilution by adding 10 μl from the boiled, concentrated extract to 90 μl of sterile dH$_2$O.

(9) Stored the diluted extracts on ice until ready to use.

Although the examples set forth herein describe using leaf tissue as the source of DNA, other plant tissue such as stem and root tissue could also be used in the above DNA extraction methods.

Example 4
Polymerase Chain Reaction Amplification

Polymerase chain reactions were performed with the GeneAmp Kit from Perkin-Elmer/Cetus (Norwalk, Conn.; part no. N808-0009) using 50 mM KCl, 2.5 mM MgCl$_2$, 10 mM Tris-HCl, pH8.3, containing 200 μM of each dTTP, dATP, dCTP, and dGTP, 50 pmol each primer, 2.5 units of Taq polymerase and 10 ng of genomic DNA or 1 μl of 1:10 diluted plant extract in a final volume of 50 μl. Reactions were run for 30–40 cycles of 15 s at 94° C., 15 s at 50° C.–70° C., and 45 s at 72° C. in a Perkin-Elmer/Cetus Model 9600 thermal cycler. The products were analyzed by loading 10 μl of each PCR sample on a 1.0% agarose gel and electrophoresed.

Example 5
Synthesis and Purification of Oligonucleotides

Oligonucleotides (primers) were synthesized by either Integrated DNA Technologies (Coralville, Iowa) or Midland Certified Reagent Company (Midland, Tex.).

Example 6
Selection of Species-Specific Primers

The ITS regions of *H. turcicum, H. maydis, H. carbonum* and *C. zeae-maydis*were aligned. Separate alignments were also made for each pathogen's isolates' ITS regions. Oligonucleotide primers (Table 2) were synthesized according to Example 5 based on analysis of the aligned sequences. Primers were designed to the regions that contained the greatest differences in sequence among the fungal species. In addition, the published ribosomal gene-specific primers ITS1, ITS2, ITS3 and ITS4 (White et al., 1990; In: PCR Protocols; Eds.: Innes et al. pages 315–322) were synthesized for testing in combination with the primers specific for the ITS region. Primers specific to the ITS regions of the published *Puccinia sorghi* sequence (Genbank accession#L08734, SEQ ID: 8) were also synthesized.

TABLE 2

Primer Design for Fungal Detection

| Primer Template | Primer Name | Primer Seguence |
|---|---|---|
| *H. turcicum* | JB586 | 5' TGGCAATCAGTGCTCTGCTG 3' (SEQ ID NO:15) |
| *H. turcicum* | JB595 | 5' TCCGAGGTCAAAATGTGAGAG 3' (SEQ ID NO:24) |
| *H. maydis* | JB589 | 5' CCTTTTTTTTATGCAGTTGCA 3' (SEQ ID NO:18) |
| *H. maydis* | JB591 | 5' CTCCTGATACAGAGTGCAAAA 3' (SEQ ID NO:20) |
| *H. maydis* | JB596 | 5' GAGGTCAAAAGTTAAAAATCGTAA 3' (SEQ ID NO:25) |
| Helmin. spp. | JB588 | 5' CACCCATGTCTTTTGCGCAC 3' (SEQ ID NO:17) |
| Helmin. spp. | JB587 | 5' CAGTTGCAATCAGCGTCAGTA 3' (SEQ ID NO:16) |
| *H. carbonum* | JB592 | 5' CTCCTGATACAAAGCGCAAAT 3' (SEQ ID NO:21) |
| *H. carbonum* | JB590 | 5' CCTTTTTTTTATGCAGTTACC 3' (SEQ ID NO:19) |
| *H. carbonum* | JB598 | 5' CCGAGGTCAAAAGTTAAAAATCTA 3' (SEQ ID NO:27) |
| *H. carbonum* | JB597 | 5' GGCTCCAGTTTTCAATTTTTAGAT 3' (SEQ ID NO:26) |
| *K. zeae* | JB616 | 5' TGTTGTTAAAACTACCTTGTTGC 3' (SEQ ID NO:29) |
| *K. zeae* | JB618 | 5' GTTTCTGTCGGCAGAAGTC 3' (SEQ ID NO:31) |
| *K. zeae* | JB615 | 5' TTTGGCGGGACCGCTCGG 3' (SEQ ID NO:28) |
| *K. zeae* | JB617 | 5' GAGTTAAACCAAACTCTTGTTG 3' (SEQ ID NO:30) |
| *K. zeae* | JB619 | 5' CGCCAGACGTTGATTGAATG 3' (SEQ ID NO:32) |
| *C. zeae-maydis* | JB593 | 5' GGCCTTCGGGCTCGACCT 3' (SEQ ID NO:22) |
| *C. zeae-maydis* | JB594 | 5' CGGACAGCTCAGCCGGAG 3' (SEQ ID NO:23) |
| *C. zeae-maydis* | JB620 | 5' CAACCCTTTGTGAACACAAC 3' (SEQ ID NO:33) |
| *C. zeae-maydis* | JB621 | 5' CGCTCCGAAGCGATTAATG 3' (SEQ ID NO:34) |
| *C. zeae-maydis* | JB622 | 5' TTCAAACACTGCATCTTTGCG 3' (SEQ ID NO:35) |

TABLE 2-continued

Primer Design for Fungal Detection

| Primer Template | Primer Name | Primer Seguence |
|---|---|---|
| *C. zeae-maydis* | JB623 | 5' AGATTTAGACGGCCGCGAC 3' (SEQ ID NO:36) |
| *C. zeae-maydis* | JB626 | 5' GAGTGAGGGCCTTCGGGC 3' (SEQ ID NO:39) |
| *C. zeae-maydis* | JB627 | 5' GCTTCGGGGGGCGACCC 3' (SEQ ID NO:40) |
| *C. zeae-maydis* | JB628 | 5' GACCGCCCGCGCTCCG 3' (SEQ ID NO:41) |
| *P. sorghi* | JB624 | 5' GTAGTCTCTATCTCAACAAC 3' (SEQ ID NO:37) |
| *P. sorghi* | JB625 | 5' GTAAACAACCACCTTTAATTAT 3' (SEQ ID NO:38) |
| 18S rDNA | ITS1 | 5' TCCGTAGGTGAACCTGCGG 31 (SEQ ID NO:9) |
| 5.8S rDNA | ITS2 | 5' GCTGCGTTCTTCATCGATGC 3' (SEQ ID NO:10) |
| 5.8S rDNA | ITS3 | 5' GCATCGATGAAGAACGCAGC 3' (SEQ ID NO:11) |
| 25S rDNA | ITS4 | 5' TCCTCCGCTTATTGATATGC 3' (SEQ ID NO:12) |

Note: Helminthosporium spp. includes *H. maydis, H. turcicum* and *H. carbonum.*

Example 7

Determination of Primer Specificity to Purified Fungal Genomic DNA

PCRs were performed according to Example 4 using different primer combinations (Table 3) in an attempt to amplify a single species-specific fragment. Species-specific PCR amplification products were produced from primers designed from the ITS region between the 18S and 25S ribosomal DNA subunits of each fungal strain of interest.

TABLE 3

ITS-Derived Diagnostic PCR Primers

| Source of template DNA | 5'Primer | 3'Primer | Approximate size of amplified fragment |
|---|---|---|---|
| *H. turcicum* | JB586 (SEQ ID NO:15) | JB595 (SEQ ID NO:24) | 485bp |
| *H. maydis* | JB589 (SEQ ID NO:18) | JB591 (SEQ ID NO:20) | 346bp |
| *H. maydis* | JB589 (SEQ ID NO:18) | JB596 (SEQ ID NO:25) | 397bp |
| *H. maydis* | JB588 (SEQ ID NO:17) | JB596 (SEQ ID NO:25) | 463bp |
| *H. maydis* | JB588 (SEQ ID NO:17) | JB591 (SEQ ID NO:20) | 413bp |
| *H. maydis* | JB587 (SEQ ID NO:16) | JB596 (SEQ ID NO:25) | 331bp |
| *H. maydis* | JB587 (SEQ ID NO:16) | JB591 (SEQ ID NO:20) | 333bp |
| *H. maydis* | JB588 (SEQ ID NO:17) | JB598 (SEQ ID NO:27) | 465bp |
| *H. maydis* | JB587 (SEQ ID NO:16) | JB598 (SEQ ID NO:27) | 375bp |
| *H. carbonum* | JB590 (SEQ ID NO:19) | JB598 (SEQ ID NO:27) | 398bp |
| *H. carbonum* | JB590 (SEQ ID NO:19) | JB592 (SEQ ID NO:21) | 346bp |
| *H. carb./H. maydis* | JB588) (SEQ ID NO:17) | JB598 (SEQ ID NO:27) | 465bp |
| *H. carb./H. maydis* | JB587 (SEQ ID NO:16) | JB598 (SEQ ID NO:27) | 384bp |

TABLE 3-continued

ITS-Derived Diagnostic PCR Primers

| Source of template DNA | 5'Primer | 3'Primer | Approximate size of amplified fragment |
|---|---|---|---|
| K. zeae | JB616 (SEQ ID NO:29) | JB618 (SEQ ID NO:31) | 455bp |
| K. zeae | JB615 (SEQ ID NO:28) | ITS4 (SEQ ID NO:12) | 508bp |
| K. zeae | JB616 (SEQ ID NO:29) | ITS4 (SEQ ID NO:12) | 531bp |
| K. zeae | JB617 (SEQ ID NO:30) | ITS4 (SEQ ID NO:12) | 443bp |
| K. zeae | JB615 (SEQ ID NO:28) | JB618 (SEQ ID NO:31) | 433bp |
| K. zeae | JB617 (SEQ ID NO:30) | JB618 (SEQ ID NO:31) | 366bp |
| K. zeae | JB615 (SEQ ID NO:28) | JB619 (SEQ ID NO:32) | 402bp |
| C. zeae-maydis | JB593 (SEQ ID NO:22) | JB594 (SEQ ID NO:23) | 380bp |
| C. zeae-maydis | JB620 (SEQ ID NO:33) | JB621 (SEQ ID NO:34) | 393bp |
| C. zeae-maydis | JB620 (SEQ ID NO:33) | JB623 (SEQ ID NO:36) | 420bp |
| C. zeae-maydis | JB622 (SEQ ID NO:35) | JB621 (SEQ ID NO:34) | 320bp |
| C. zeae-maydis | JB593 (SEQ ID NO:22) | JB621 (SEQ ID NO:34) | 415bp |
| C. zeae-maydis | JB622 (SEQ ID NO:35) | JB594 (SEQ ID NO:23) | 285bp |
| C. zeae-maydis | JB593 (SEQ ID NO:22) | JB623 (SEQ ID NO:36) | 442bp |
| C. zeae-maydis | JB626 (SEQ ID NO:39) | JB628 (SEQ ID NO:41) | 427bp |
| C. zeae-maydis | JB593 (SEQ ID NO:22) | ITS4 (SEQ ID NO:12) | 558bp |
| P. sorghi | JB624 (SEQ ID NO:37) | JB625 (SEQ ID NO:38) | 409bp |
| P. sorghi/Helm.spp. | JB587 (SEQ ID NO:16) | ITS4 (SEQ ID NO:12) | 434bp |
| P. sorghi/Helm.spp. | JB588 (SEQ ID NO:17) | ITS4 (SEQ ID NO:12) | 517bp |

Note: Helminthosporium spp. includes H. maydis, H. turcicum and H. carbonum.

Example 8
Determination of Primer Specificity to Plant Tissue Infected with Fungi and Cross-Reactivity with Other Maize Fungal Pathogens Total genomic DNA was isolated as described in Example 3 from healthy maize leaves and from maize leaves inoculated with either H. turcicum, H. maydis, H. carbonum, K. zeae, C. zeae-maydis or P. sorghi. PCRs were performed as described in Example 4 testing the primer combinations listed in Example 7 against DNA from the maize leaves. Purified fungal genomic DNAs were obtained as described in Example 1 and PCR assayed as described in Example 4 using the species-specific primers. Other fungal DNA species and isolates were tested for the species-specific primers ability to cross-react with them.

The H. turcicum-specific primers JB586 (SEQ ID NO:15) and JB595 (SEQ ID NO:24) amplified a 485 bp fragment from DNA from all of the isolates of H. turcicum listed in Table 1 and from H. turcicum-infected maize leaf tissue. The primer set did not amplify a diagnostic fragment from healthy maize leaf tissue nor from purified genomic DNA from H. maydis, H. carbonum, K. zeae, C. zeae-maydis and P. sorghi. The primers also did not amplify a diagnostic fragment from purified genomic DNA isolated from the common maize pathogens F. monililforme, M. phaseolina, A. flavus nor D. maydis.

Similar diagnostic results were obtained with the H. maydis-specific primers JB589 (SEQ ID NO:18) and JB591 (SEQ ID NO:20). The primers amplified an approximately 346 bp fragment from H. maydis-infected maize tissue, as well as from purified genomic DNA isolated from all of the H. maydis isolates listed in Table 1. The primer combination JB589 and JB591 did not amplify any fragments from healthy maize tissue, nor from DNA from any of the following maize pathogens: H. turcicum, H. carbonum, K. zeae, C. zeae-maydis, P. sorghi, F. moniliforme, M. phaseolina, A. flavus and D. maydis.

The primer combination JB590 (SEQ ID NO:19) and JB598 (SEQ ID NO:27) amplified a 398 bp fragment from DNA from all of the H. carbonum isolates listed in Table 1 and from maize leaves infected with H. carbonum. The primer combination JB590 and JB598 did not amplify any fragments from healthy maize tissue, nor from DNA from any of the following maize pathogens: H. turcicum, H. maydis, K. zeae, C. zeae-maydis, P. sorghi, F. moniliforme, M. phaseolina, A. flavus and D. maydis.

The K. zeae-specific primers JB616 (SEQ ID NO:29) and JB618 (SEQ ID NO:31) amplified a 455 bp fragment from DNA from all of the isolates of K. zeae isolates listed in Table 1 and from K. zeae-infected maize leaf tissue. The primer set did not amplify a diagnostic fragment from healthy maize leaf tissue nor from purified genomic DNA from H. maydis, H. carbonum, H. turcicum, C. zeae-maydis and P. sorghi. The primers also did not amplify a diagnostic fragment from purified genomic DNA isolated from the common maize pathogens F. monililfonne, M. phaseolina, A. flavus nor D. maydis.

The primer combination JB593 (SEQ ID NO:22) and JB621 (SEQ ID NO:34) amplified a 415 bp fragment from DNA from all of the C. zeae-maydis isolates listed in Table 1 and from maize leaves infected with C. zeae-maydis. The primer combination JB593 and JB621 did not amplify any fragments from healthy maize tissue, nor from DNA from any of the following maize pathogens: H. turcicum, H. maydis, K. zeae, H. carbonum, P. sorghi, F. moniliforme, M. phaseolina, A. flavus and D. maydis.

The primer combination JB624 (SEQ ID NO:37) and JB625 (SEQ ID NO:38) amplified a 409 bp fragment from all of the P. sorghi isolates listed in Table 1 and from P. sorghi-infected maize leaf tissue. The primers did not amplify from P. polyspora, H. turcicum, H. maydis, K. zeae, H. carbonum, F. moniliforme, M. phaseolina, A. flavus and D. maydis. The primers also did not amplify from healthy maize tissue.

Primers JB587 (SEQ ID NO:16) and ITS4 (SEQ ID NO:12) amplified a 434 bp fragment from P. sorghi, H. turcicum, H. maydis and H. carbonum but not from the other following maize pathogens: K. zeae, F. moniliforme, M. phaseolina, A. flavus and D. maydis. The primers also amplified a 434 bp fragment from maize infected with P. sorghi, H. turcicum, H. maydis and H. carbonum but did not amplify any fragments from healthy maize tissue.

While the present invention has been described with reference to specific embodiments thereof, it will be appreciated that numerous variations, modifications, and further embodiments are possible, and accordingly, all such variations, modifications and embodiments are to be regarded as being within the scope of the present invention.

DEPOSITS

The following deposits were made on Nov. 6, 1996, at Agricultural Research Service, Patent Culture Collection (NRRL), Northern Regional Research Center, 1815 North University Street, Peoria, Ill. 61604, U.S.A.:
1. E. coli DH5α (pCRCZLAD3-1(4-3); SEQ ID NO:1): Accession No. NRRL B-21645.

2. *E. coli* DH5α (pCRCZMPOS12(2-1); SEQ ID NO:2): Accession No. NRRL B-21641.
3. *E. coli* DH5α (pCRKZ56351(5-1); SEQ ID NO:3): Accession No. NRRLB-21646.
4. *E. coli* DH5α (pCRHMAY24772(2-1); SEQ ID NO:4): Accession No. NRRL B-21642.
5. *E. coli* DH5α (pCRHMAY11534(4-1); SEQ ID NO:5): Accession No. NRRL B-21644.
6. *E. coli* DH5α (pCRHTUR26306(3-1); SEQ ID NO:6): Accession No. NRRL B-21643.
7. *E. coli* DH5α (pCRHCAR16185(5-2); SEQ ID NO:7): Accession No. NRRL B-21647.

What is claimed is:

1. A DNA extraction buffer, comprising:
   (a) approximately 0.1% w/v Tween-80;
   (b) approximately 0.04 M Tris-Cl, pH 6–8;
   (c) 0.15–2.0 M NaCl;
   (d) approximately 0.1% BSA;
   (e) approximately 0.01% sodium azide; and
   (f) 180–500 mM EDTA.

2. The extraction buffer of claim 1, comprising: 0.1% w/v Tween-80; 0.04 M Tris-Cl, pH 7.7; 0.15 M NaCl; 0.1% w/v BSA-Pentex fraction V; 0.01% w/v sodium azide; and 200 mM EDTA.

3. The extraction buffer of claim 1, further comprising 0–2% w/v tartrazin.

4. A method for preparing an extract of DNA from tissue, comprising the steps of:
   (a) taking a plurality of random tissue samples from an organism population;
   (b) adding the extraction buffer of claim 1 to the tissue samples;
   (c) macerating the tissue samples and extraction buffer to form an extract; and
   (d) removing the extract from the macerated tissue and buffer.

5. The method of claim 4, wherein the organism population is a plant population.

6. The method of claim 5, wherein the tissue samples are selected from leaves, stems, and roots.

7. The method of claim 4, wherein the extraction buffer comprises 0.1% w/v Tween-80; 0.04 M Tris-Cl, pH 7.7; 0.15 M NaCl; 0.1% w/v BSA-Pentex fraction V; 0.01% w/v sodium azide; and 200 mM EDTA.

8. A method for performing PCR analysis on DNA extracted from tissue, comprising the steps of:
   (a) taking a plurality of random tissue samples from an organism population;
   (b) adding the extraction buffer of claim 1 to the tissue samples;
   (c) macerating the tissue samples and extraction buffer to form an extract;
   (d) removing the extract from the macerated tissue and buffer; and
   (e) performing PCR analysis on the extract.

9. The method of claim 8, further comprising the step of boiling the extract after removing it from the macerated tissue and buffer.

10. The method of claim 9, further comprising the step of diluting the extract.

11. The method of claim 10, wherein the organism population is a plant population.

12. The method of claim 11, wherein the tissue samples are selected from leaves, stems, and roots.

13. The method of claim 8, wherein the extraction buffer comprises 0.1% w/v Tween-80; 0.04 M Tris-Cl, pH 7.7; 0.15 M NaCl; 0.1% w/v BSA-Pentex fraction V; 0.01% w/v sodium azide; and 200 mM EDTA.

14. The DNA extraction buffer of claim 1, comprising 0.1% w/v Tween-80.

15. The DNA extraction buffer of claim 1, comprising 0.04 M Tris-Cl, pH 6–8.

16. The DNA extraction buffer of claim 1, comprising 0.15 M NaCl.

17. The DNA extraction buffer of claim 1, comprising 0.1% BSA.

18. The DNA extraction buffer of claim 1, comprising 0.01% sodium azide.

19. The DNA extraction buffer of claim 1, comprising 200 mM EDTA.

* * * * *

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
(A) LENGTH: 535 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(B) STRAIN: Cercospora zeae-maydis
(C) INDIVIDUAL ISOLATE: Ladder 3-1

(vii) IMMEDIATE SOURCE:
(B) CLONE: pCRCZLAD3-1(4-3)

(ix) FEATURE:
(A) NAME/KEY: misc_RNA
(B) LOCATION: 1..30
(D) OTHER INFORMATION: /note= "3' end of small subunit rRNA gene"

(ix) FEATURE:
(A) NAME/KEY: misc_feature
(B) LOCATION: 31..175
(D) OTHER INFORMATION: /note= "ITS 1"

(ix) FEATURE:
(A) NAME/KEY: misc_RNA
(B) LOCATION: 176..332
(D) OTHER INFORMATION: /note= "5.8S rRNA gene"

(ix) FEATURE:
(A) NAME/KEY: misc_feature
(B) LOCATION: 333..478
(D) OTHER INFORMATION: /note= "ITS 2"

(ix) FEATURE:
(A) NAME/KEY: misc_RNA
(B) LOCATION: 479..535
(D) OTHER INFORMATION: /note= "5' end of large subunit rRNA gene"

(xi) SEQUENCE DESCRIPTION: SEQ ID NO:1:

```
TCCGTAGGTG AACCTGCGGA GGGATCATTA CTGAGTGAGG GCCTTCGGGC TCGACCTCCA     60

ACCCTTTGTG AACACAACTT GTTGCTTCGG GGGCGACCCT GCCGTTCCGA CGGCGAGCGC    120

CCCCGGAGGC CTTCAAACAC GCATCTTTGC GTCGGAGTTT AAGTAAATTA AACAAAACTT    180

TCAACAACGG ATCTCTTGGT TCTGGCATCG ATGAAGAACG CAGCGAAATG CGATAAGTAA    240

TGTGAATTGC AGAATTCAGT GAATCATCGA ATCTTTGAAC GCATATTGCG CCCTTTGGTA    300

TTCCGAAGGG CATGCCTGTT CGAGCGTCAT TTCACCACTC AAGCCTAGCT TGGTACTGGG    360

CGCCGCGGTG TTCCGCGCGC CTTAAAGTCT CCGGCTGAGC TGTCCGTCTC TAAGCGTTGT    420

GATTTCATTA ATCGCTTCGG AGCGCGGGCG GTCGCGGCCG TTAAATCTTT CACAAGGTTG    480

ACCTCGGATC AGGTAGGGAT ACCCGCTGAA CTTAAGCATA TCAATAAGCG GAGGA         535
```

(2) INFORMATION FOR SEQ ID NO:2:

(i) SEQUENCE CHARACTERISTICS:
        (A) LENGTH: 536 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Cercospora zeae-maydis
        (C) INDIVIDUAL ISOLATE: POS 12

(vii) IMMEDIATE SOURCE:
        (B) CLONE: pCRCZMPOS12(2-1)

(ix) FEATURE:
        (A) NAME/KEY: misc_RNA
        (B) LOCATION: 1..30
        (D) OTHER INFORMATION: /note= "3' end of small subunit
            rRNA gene"

(ix) FEATURE:
        (A) NAME/KEY: misc_feature
        (B) LOCATION: 31..176
        (D) OTHER INFORMATION: /note= "ITS 1"

(ix) FEATURE:
        (A) NAME/KEY: misc_RNA
        (B) LOCATION: 177..333
        (D) OTHER INFORMATION: /note= "5.8S rRNA gene"

(ix) FEATURE:
        (A) NAME/KEY: misc_feature
        (B) LOCATION: 334..479
        (D) OTHER INFORMATION: /note= "ITS 2"

(ix) FEATURE:
        (A) NAME/KEY: misc_RNA
        (B) LOCATION: 480..536
        (D) OTHER INFORMATION: /note= "5' end of large subunit
            rRNA gene"

(xi) SEQUENCE DESCRIPTION: SEQ ID NO:2:

```
TCCGTAGGTG AACCTGCGGA GGGATCATTA CTGAGTGAGG GCCTTCGGGC TCGACCTCCA      60

ACCCTTTGTG AACACAACTT GTTGCTTCGG GGGCGACCCT GCCGTTCCGA CGGCGAGCGC     120

CCCCGGAGGC CTTCAAACAC TGCATCTTTG CGTCGGAGTT TAAGTAAATT AAACAAAACT     180

TTCAACAACG GATCTCTTGG TTCTGGCATC GATGAAGAAC GCAGCGAAAT GCGATAAGTA     240

ATGTGAATTG CAGAATTCAG TGAATCATCG AATCTTTGAA CGCATATTGC GCCCTTTGGT     300

ATTCCGAAGG GCATGCCTGT TCGAGCGTCA TTTCACCACT CAAGCCTAGC TTGGTATTGG     360

GCGCCGCGGT GTTCCGCGCG CCTTAAAGTC TCCGGCTGAG CTGTCCGTCT CTAAGCGTTG     420

TGATTTCATT AATCGCTTCG GAGCGCGGGC GGTCGCGGCC GTTAAATCTT TCACAAGGTT     480

GACCTCGGAT CAGGTAGGGA TACCCGCTGT ACTTAAGCAT ATCAATAAGC GGAGGA         536
```

(2) INFORMATION FOR SEQ ID NO:3:

(i) SEQUENCE CHARACTERISTICS:
        (A) LENGTH: 597 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Kabatiella zeae (C) INDIVIDUAL ISOLATE: 56351

(vii) IMMEDIATE SOURCE:
        (B) CLONE: pCRKZ56351(5-1)

(ix) FEATURE:
        (A) NAME/KEY: misc_RNA
        (B) LOCATION: 1..30
        (D) OTHER INFORMATION: /note= "3' end of small subunit
            rRNA gene"

(ix) FEATURE:
        (A) NAME/KEY: misc_feature
        (B) LOCATION: 31..217
        (D) OTHER INFORMATION: /note= "ITS 1"

(ix) FEATURE:
        (A) NAME/KEY: misc_RNA
        (B) LOCATION: 218..373
        (D) OTHER INFORMATION: /note= "5.8S rRNA gene"

(ix) FEATURE:
        (A) NAME/KEY: misc_feature
        (B) LOCATION: 374..540
        (D) OTHER INFORMATION: /note= "ITS 2"

(ix) FEATURE:
        (A) NAME/KEY: misc_RNA
        (B) LOCATION: 541..597
        (D) OTHER INFORMATION: /note= "5' end of large subunit
            rRNA gene"

(xi) SEQUENCE DESCRIPTION: SEQ ID NO:3:

```
TCCGTAGGTG AACCTGCGGA AGGATCATTA AAGAGTAAGG GTGCCCAGCG CCCGACCTCC      60

AACCCTTTGT TGTTAAAACT ACCTTGTTGC TTTGGCGGGA CCGCTCGGTC CCCGAGCCGC     120

CGGGGGGATC CGTCCCCCAT GGCGAGCGCC CGCCGGAGTT AAACCAAACT CTTGTTGAAC     180

AAACCGGTCG TCTGAGTTAA AATTTTGAAT AAATCAAAAC TTTCAACAAC GGATCTCTTG     240

GTTCTCGCAT CGATGAAGAA CGCAGCGAAA TGCGATAAGT AATGTGAATT GCAGAATTCA     300

GTGAATCATC GAATCTTTGA ACGCACATTG CGCCCCTTGG TATTCCGAGG GGCATGCCTG     360

TTCGAGCGTC ATTACACCAC TCAAGCTCTG CTTGGTATTG GGCGTCCGTC CTTTCGGGGG     420

CGCGCCTCAA ACACCTCGGC GAGGCCTCAC CGGCTTCAGG CGTAGTAGAA TTCATTCAAT     480

CAACGTCTGG CGAAACCGGA GGGGACTTCT GCCGACAGAA ACCTTTTATA TTTTCTAGGT     540

TGACCTCGGA TCAGGTAGGG ATACCCGCTG AACTTAAGCA TATCAATAAG CGGAGGA       597
```

(2) INFORMATION FOR SEQ ID NO:4:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Helminthosporium maydis
        (C) INDIVIDUAL ISOLATE: 24772

(vii) IMMEDIATE SOURCE:
        (B) CLONE: pCRHMAY24772(2-1)

(ix) FEATURE:
        (A) NAME/KEY: misc_RNA
        (B) LOCATION: 1..30
        (D) OTHER INFORMATION: /note= "3' end of small subunit
            rRNA gene"

(ix) FEATURE:

(A) NAME/KEY: misc_feature
            (B) LOCATION: 31..200
            (D) OTHER INFORMATION: /note= "ITS 1"

(ix) FEATURE:
            (A) NAME/KEY: misc_RNA
            (B) LOCATION: 201..358
            (D) OTHER INFORMATION: /note= "5.8S rRNA gene"

(ix) FEATURE:
            (A) NAME/KEY: misc_feature
            (B) LOCATION: 359..531
            (D) OTHER INFORMATION: /note= "ITS 2"

(ix) FEATURE:
            (A) NAME/KEY: misc_RNA
            (B) LOCATION: 532..588
            (D) OTHER INFORMATION: /note= "5' end of large subunit
                rRNA gene"

(xi) SEQUENCE DESCRIPTION: SEQ ID NO:4:

```
TCCGTAGGTG AACCTGCGGA GGGATCATTA CACAACAAAA TATGAAGGCC TGGCTTTGCG      60

GCCGGCTGAA ATATTTTTTT CACCCATGTC TTTTGCGCAC TTGTTGTTTC CTGGGCGGGT     120

TCGCCCGCCA CCAGGACCAA ACCCTAAACC TTTTTTTTAT GCAGTTGCAW TCAGCGTCAG     180

TATAAACAAT GTAATTATTA CAACTTTCAA CAACGGATCT CTTGGTTCTG GCATCGATGA     240

AGAACGCAGC GAAATGCGAT ACGTAGTGTG AATTGCAGAA TTCAGTGAAT CATCGAATCT     300

TTGAACGCAC ATTGCGCCCT TGGTATTCC AAAGGGCATG CCTGTTCGAG CGTCATTTGT      360

ACCCTCAAGC TTTGCTTGGT GTTGGGCGTT TTTGTCTCCC TCTTTGCTGG GAGACTCGCC     420

TTAAAACGAW TGGCAGCCGG CCTACTGGTT TCGGAGCGCA GCACATATTT TGCACTCTGT     480

ATCAGGAGAA AAGGACGGTA ATCCATCAAG ACTCTTACGA TTTTTAACTT TTGACCTCGG     540

ATCAGGTAGG GAYACCCGCT GAACTTAAGC ATATCAATAA GCGGAGGA                 588
```

(2) INFORMATION FOR SEQ ID NO:5:

(i) SEQUENCE CHARACTERISTICS:
            (A) LENGTH: 588 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (B) STRAIN: Helminthosporium maydis
            (C) INDIVIDUAL ISOLATE: 11534

(vii) IMMEDIATE SOURCE:
            (B) CLONE: pCRHMAY11534(4-1)

(ix) FEATURE:
            (A) NAME/KEY: misc_RNA
            (B) LOCATION: 1..30
            (D) OTHER INFORMATION: /note= "3' end of small subunit
                rRNA gene"

(ix) FEATURE:
            (A) NAME/KEY: misc_feature
            (B) LOCATION: 31..200
            (D) OTHER INFORMATION: /note= "ITS 1"

(ix) FEATURE:
            (A) NAME/KEY: misc_RNA
            (B) LOCATION: 201..358
            (D) OTHER INFORMATION: /note= "5.8S rRNA gene"

(ix) FEATURE:
            (A) NAME/KEY: misc_feature
            (B) LOCATION: 359..531

(D) OTHER INFORMATION: /note= "ITS 2"

(ix) FEATURE:
    (A) NAME/KEY: misc_RNA
    (B) LOCATION: 532..588
    (D) OTHER INFORMATION: /note= "5' end of large subunit
        rRNA gene"

(xi) SEQUENCE DESCRIPTION: SEQ ID NO:5:

```
TCCGTAGGTG AACCTGCGGA GGGATCATTA CACAACAAAA TATGAAGGCC TGGCTTTGCG     60

GCCGGCTGAA ATATTTTTTT CACCCATGTC TTTTGCGCAC TTGTTGTTTC CTGGGCGGGT    120

TCGCCCGCCA CCAGGACCAA ACCATAAACC TTTTTTTTAT GCAGTTGCAA TCAGCGTCAG    180

TATAAACAAT GTAATTATTA CAACTTTCAA CAACGGATCT CTTGGTTCTG GCATCGATGA    240

AGAACGCAGC GAAATGCGAT ACGTAGTGTG AATTGCAGAA TTCAGTGAAT CATCGAATCT    300

TTGAACGCAC ATTGCGCCCT TTGGTATTCC AAAGGGCATG CCTGTTCGAG CGTCATTTGT    360

ACCCTCAAGC TTTGCTTGGT GTTGGGCGTT TTTGTCTCCC TCTTTGCTGG GAGACTCGCC    420

TTAAAACGAT TGGCAGCCGG CCTACTGGTT TCGGAGCGCA GCACATATTT TGCACTCTGT    480

ATCAGGAGAA AAGGACGGTA ATCCATCAAG ACTCTTACGA TTTTTAACTT TTGACCTCGG    540

ATCAGGTAGG GATACCCGCT GAACTTAAGC ATATCAATAA GCGGAGGA                 588
```

(2) INFORMATION FOR SEQ ID NO:6:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Helminthosporium turcicum
        (C) INDIVIDUAL ISOLATE: 26306

(vii) IMMEDIATE SOURCE:
        (B) CLONE: pCRHTUR26306(3-1)

(ix) FEATURE:
        (A) NAME/KEY: misc_RNA
        (B) LOCATION: 1..30
        (D) OTHER INFORMATION: /note= "3' end of small subunit
            rRNA gene"

(ix) FEATURE:
        (A) NAME/KEY: misc_feature
        (B) LOCATION: 31..199
        (D) OTHER INFORMATION: /note= "ITS 1"

(ix) FEATURE:
        (A) NAME/KEY: misc_RNA
        (B) LOCATION: 200..356
        (D) OTHER INFORMATION: /note= "5.8S rRNA gene"

(ix) FEATURE:
        (A) NAME/KEY: misc_feature
        (B) LOCATION: 357..523
        (D) OTHER INFORMATION: /note= "ITS 2"

(ix) FEATURE:
        (A) NAME/KEY: misc_RNA
        (B) LOCATION: 524..580
        (D) OTHER INFORMATION: /note= "5' end of large subunit
            rRNA gene"

(xi) SEQUENCE DESCRIPTION: SEQ ID NO:6:

```
TCCGTAGGTG AACCTGCGGA GGGATCATTA CACAAAGATA TGAAGGTAGG GTACTGGCAA     60
```

```
CAGTGCTCTG CTGAAATATT TTCACCCATG TCTTTTGCGC ACTTTTTGTT TCCTGGGCGA      120

GTTTGCTCGC CACCAGGACC CCCATATGAA CCTTTTTTGT TTTTGCACTC AGCGTCAGTA      180

CAATAATTTA ATCTATTAAA ACTTTCAACA ACGGATCTCT TGGTTCTGGC ATCGATGAAG      240

AACGCAGCGA AATGCGATAC GTAGTGTGAA TTGCAGAATT CAGTGAATCA TCGAATCTTT      300

GAACGCACAT TGCGCCCTTT GGTATTCCAA AGGGCATGCC TGTTCGAGCG TCATTTGTAC      360

CCTCAAGCTT TGCTTGGTGT TGGGCGTCTT ATTGTCTCTC CGTCTCGGGG AGACTCGCCT      420

TAAAACAATT GGCAGCCGGC CTACTGGTTT CGGAGCGCAG CACAAATTTG CGCTTGCAAT      480

CAGCCAAGGG CGGCATCCAT GAAGCCTTTT TTCTCTCACA TTTTGACCTC GGATCAGGTA      540

GGGATACCCG CTGAACTTAA GCATATCAAT AAGCGGAGGA                           580

(2) INFORMATION FOR SEQ ID NO:7:

(i) SEQUENCE CHARACTERISTICS:
        (A) LENGTH: 587 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Helminthosporium carbonum
        (C) INDIVIDUAL ISOLATE: 16185

(vii) IMMEDIATE SOURCE:
        (B) CLONE: pCRHCAR16185(5-2)

(ix) FEATURE:
        (A) NAME/KEY: misc_RNA
        (B) LOCATION: 1..30
        (D) OTHER INFORMATION: /note= "3' end of small subunit
            rRNA gene"

(ix) FEATURE:
        (A) NAME/KEY: misc_feature
        (B) LOCATION: 31..202
        (D) OTHER INFORMATION: /note= "ITS 1"

(ix) FEATURE:
        (A) NAME/KEY: misc_RNA
        (B) LOCATION: 203..360
        (D) OTHER INFORMATION: /note= "5.8S rRNA gene"

(ix) FEATURE:
        (A) NAME/KEY: misc_feature
        (B) LOCATION: 361..530
        (D) OTHER INFORMATION: /note= "ITS 2"

(ix) FEATURE:
        (A) NAME/KEY: misc_RNA
        (B) LOCATION: 531..587
        (D) OTHER INFORMATION: /note= "5' end of large subunit
            rRNA gene"

(xi) SEQUENCE DESCRIPTION: SEQ ID NO:7:

TCCGTAGGTG AACCTGCGGA GGGATCATTA CACAACAAAA TATGAAGGCC CTGGCTTCGC       60

GGCCGGCTGA AATATTTTTT CACCCATGTC TTTTGCGCAC TTGTTGTTTC CTGGGCGGGT      120

TTGCCCGCCA CCAGGACCAA ACCATAAACC TTTTTTTTTA TGCAGTTACC ATCAGCGTCA      180

GTAAAAACAA TGTAATTAAT TACAACTTTC AACAACGGAT CTCTTGGTTC TGGCATCGAT      240

GAAGAACGCA GCGAAATGCG ATACGTAGTG TGAATTGCAG AATTCAGTGA ATCATCGAAT      300

CTTTGAACGC ACATTGCGCC CTTTGGTATT CCAAAGGGCA TGCCTGTTCG AGCGTCATTT      360

GTACCTTCAA GCTTTGCTTG GTGTTGGGCG TTTTTGTCTC CCTCTTTCTG GGAGACTCGC      420
```

```
CTTAAAACGA TTGGCAGCCG GCCTACTGGT TTCGGAGCGC AGCACATAAT TTGCGCTTTG        480

TATCAGGAGA AAAGGACGGT AATCCATCAA GACTCTAGAT TTTTAACTTT TGACCTCGGA        540

TCAGGTAGGG ATACCCGCTG AACTTAAGCA TATCAATAAG CGGAGGA                     587
```

(2) INFORMATION FOR SEQ ID NO:8:

(i) SEQUENCE CHARACTERISTICS:
        (A) LENGTH: 458 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Puccinia sorghi
        (C) INDIVIDUAL ISOLATE: SZZI11

(ix) FEATURE:
        (A) NAME/KEY: misc_feature
        (B) LOCATION: 1..45
        (D) OTHER INFORMATION: /note= "partial ITS 1"

(ix) FEATURE:
        (A) NAME/KEY: misc_RNA
        (B) LOCATION: 46..201
        (D) OTHER INFORMATION: /note= "5.8S rRNA gene"

(ix) FEATURE:
        (A) NAME/KEY: misc_feature
        (B) LOCATION: 202..441
        (D) OTHER INFORMATION: /note= "ITS 2"

(ix) FEATURE:
        (A) NAME/KEY: misc_RNA
        (B) LOCATION: 442..458
        (D) OTHER INFORMATION: /note= "5' end of large subunit
            rRNA gene"

(xi) SEQUENCE DESCRIPTION: SEQ ID NO:8:

```
ACACAAGTTT AAAAGAATGT AAACAACCAC CTTTAATTAT AAAAATAACT TTTAACAATG         60

GATCTCTAGG CTCTCACATC GATGAAGAAC ACAGTGAAAT GTGATAAGTA ATGTGAATTG        120

CAGAATTCAG TGAATCATCG AATCTTTGAA CGCATCTTGC GCCTTTTGGT ATTCCAAAAG        180

GCACACCTGT TGAGTGTCA TGAAACCCTC TCACAAAATA AATAATTTTT ATTATGATTT        240

TTGTGGATGT TGAGTGCTGC TGTGTTACAC ATAGCTCACT TTAAATGTAT AAGTCATCTT        300

CTTTATATAG CAAAAAGAA GAGATGGATT GACTTGATGT GTAATAATTT TTTTTCATCA        360

CATTGAGGAA AGTAGCAATA CTTGCCATCT TTATATTATT TTGTTGTTGA GATAGAGACT        420

ACTAAACAAA CAATTTAAAA TTTAAGACCT CAAATCAG                               458
```

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer ITS1"

(xi) SEQUENCE DESCRIPTION: SEQ ID NO:9:

```
TCCGTAGGTG AACCTGCGG                                                     19
```

(2) INFORMATION FOR SEQ ID NO:10:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer ITS2"

(xi) SEQUENCE DESCRIPTION: SEQ ID NO:10:

GCTGCGTTCT TCATCGATGC                                               20

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer ITS3"

(xi) SEQUENCE DESCRIPTION: SEQ ID NO:11:

GCATCGATGA AGAACGCAGC                                               20

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer ITS4"

(xi) SEQUENCE DESCRIPTION: SEQ ID NO:12:

TCCTCCGCTT ATTGATATGC                                               20

(2) INFORMATION FOR SEQ ID NO:13:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "M13 universal-20 primer"

(xi) SEQUENCE DESCRIPTION: SEQ ID NO:13:

GTAAAACGAC GGCCAGT                                                  17

(2) INFORMATION FOR SEQ ID NO:14:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Reverse primer used in
                Example 2"

(xi) SEQUENCE DESCRIPTION: SEQ ID NO:14:

AACAGCTATG ACCATG                                                   16

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB586"

(xi) SEQUENCE DESCRIPTION: SEQ ID NO:15:

TGGCAATCAG TGCTCTGCTG                                     20

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB587"

(xi) SEQUENCE DESCRIPTION: SEQ ID NO:16:

CAGTTGCAAT CAGCGTCAGT A                                   21

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB588"

(xi) SEQUENCE DESCRIPTION: SEQ ID NO:17:

CACCCATGTC TTTTGCGCAC                                     20

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB589"

(xi) SEQUENCE DESCRIPTION: SEQ ID NO:18:

CCTTTTTTTT ATGCAGTTGC A                                   21

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB590"

(xi) SEQUENCE DESCRIPTION: SEQ ID NO:19:

CCTTTTTTTT TATGCAGTTA CC                                 22

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB591"

(xi) SEQUENCE DESCRIPTION: SEQ ID NO:20:

CTCCTGATAC AGAGTGCAAA A        21

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB592"

(xi) SEQUENCE DESCRIPTION: SEQ ID NO:21:

CTCCTGATAC AAAGCGCAAA T        21

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB593"

(xi) SEQUENCE DESCRIPTION: SEQ ID NO:22:

GGCCTTCGGG CTCGACCT        18

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB594"

(xi) SEQUENCE DESCRIPTION: SEQ ID NO:23:

CGGACAGCTC AGCCGGAG        18

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB595"

(xi) SEQUENCE DESCRIPTION: SEQ ID NO:24:

TCCGAGGTCA AAATGTGAGA G        21

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB596"

(xi) SEQUENCE DESCRIPTION: SEQ ID NO:25:

GAGGTCAAAA GTTAAAAATC GTAA                                                24

(2) INFORMATION FOR SEQ ID NO:26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB597"

(xi) SEQUENCE DESCRIPTION: SEQ ID NO:26:

GGCTCCAGTT TTCAATTTTT AGAT                                                24

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB598"

(xi) SEQUENCE DESCRIPTION: SEQ ID NO:27:

CCGAGGTCAA AAGTTAAAAA TCTA                                                24

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB615"

(xi) SEQUENCE DESCRIPTION: SEQ ID NO:28:

TTTGGCGGGA CCGCTCGG                                                            18

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB616"

(xi) SEQUENCE DESCRIPTION: SEQ ID NO:29:

TGTTGTTAAA ACTACCTTGT TGC                                                    23

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB617"

(xi) SEQUENCE DESCRIPTION: SEQ ID NO:30:

GAGTTAAACC AAACTCTTGT TG                                                     22

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB618"

(xi) SEQUENCE DESCRIPTION: SEQ ID NO:31:

GTTTCTGTCG GCAGAAGTC                                                         19

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB619"

(xi) SEQUENCE DESCRIPTION: SEQ ID NO:32:

CGCCAGACGT TGATTGAATG                                                        20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB620"

(xi) SEQUENCE DESCRIPTION: SEQ ID NO:33:

CAACCCTTTG TGAACACAAC                                                        20

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB621"

(xi) SEQUENCE DESCRIPTION: SEQ ID NO:34:

CGCTCCGAAG CGATTAATG                                                        19

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB622"

(xi) SEQUENCE DESCRIPTION: SEQ ID NO:35:

TTCAAACACT GCATCTTTGC G                                                     21

(2) INFORMATION FOR SEQ ID NO:36:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB623"

(xi) SEQUENCE DESCRIPTION: SEQ ID NO:36:

AGATTTAGAC GGCCGCGAC                                                        19

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB624"

(xi) SEQUENCE DESCRIPTION: SEQ ID NO:37:

GTAGTCTCTA TCTCAACAAC                                                       20

(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB625"

(xi) SEQUENCE DESCRIPTION: SEQ ID NO:38:

GTAAACAACC ACCTTTAATT AT                                                    22

(2) INFORMATION FOR SEQ ID NO:39:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB626"

-continued

```
(xi) SEQUENCE DESCRIPTION: SEQ ID NO:39:

GAGTGAGGGC CTTCGGGC                                                    18

(2) INFORMATION FOR SEQ ID NO:40:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB627"

(xi) SEQUENCE DESCRIPTION: SEQ ID NO:40:

GCTTCGGGGG GCGACCC                                                     17

(2) INFORMATION FOR SEQ ID NO:41:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JB628"

(xi) SEQUENCE DESCRIPTION: SEQ ID NO:41:

GACCGCCCGC GCTCCG                                                      16
```